| United States Patent [19] | [11] Patent Number: 5,015,678 |
| Seltzer et al. | [45] Date of Patent: May 14, 1991 |

[54] STABILIZERS DERIVED FROM N-HYDROXY HINDERED AMINES BY MICHAEL ADDITION REACTIONS

[75] Inventors: Raymond Seltzer, New City; James P. Galbo, Hartsdale; Ramanathan Ravichandran, Nanuet, all of N.Y.

[73] Assignee: Ciba-Geigy Corporation, Ardsley, N.Y.

[21] Appl. No.: 480,177

[22] Filed: Feb. 14, 1990

Related U.S. Application Data

[63] Continuation-in-part of Ser. No. 326,354, Mar. 21, 1989, abandoned.

[51] Int. Cl.$^5$ .............. C08K 5/3435; C07D 211/34; C07D 211/40; C07D 211/54
[52] U.S. Cl. ..................... 524/99; 524/102; 524/103; 546/17; 546/22; 546/24; 546/187; 546/188; 546/190; 546/203; 546/205; 546/207; 546/214; 546/217; 546/242; 546/244
[58] Field of Search .............. 524/102, 99, 103; 546/188, 17, 22, 24, 187, 190, 203, 205, 214, 217, 207, 242, 244

[56] References Cited

U.S. PATENT DOCUMENTS

| 4,426,472 | 1/1984 | Berner ................... 524/99 |
| 4,753,972 | 6/1988 | Ravichandran ............ 524/131 |
| 4,757,102 | 7/1988 | Ravichandran et al. ...... 524/131 |

OTHER PUBLICATIONS

Shlyapintokh et al., "Developments in Polymer Stabilisation", 5, 41–70, 1982, G. Moad et al., Aust J. Chem., 36 1573 (1983).

*Primary Examiner*—Kriellion Morgan
*Attorney, Agent, or Firm*—Luther A. R. Hall

[57] ABSTRACT

The Michael addition products of N-hydroxy hindered amines with alpha,beta-unsaturated carbonyl compounds including derivatives of esters, amids, imides and anhydrides are effective stabilizers for protecting organic polymers from the deleterious effects of actinic light.

37 Claims, No Drawings

STABILIZERS DERIVED FROM N-HYDROXY HINDERED AMINES BY MICHAEL ADDITION REACTIONS

This is a continuation-in-part of application Ser. No. 326,354, filed on Mar. 21, 1989, now abandoned.

The Michael addition products of N-hydroxy hindered amines with alpha,beta-unsaturated carbonyl compounds are effective light stabilizers for organic polymers.

BACKGROUND OF THE INVENTION

The Michael addition product of 4-benzyloxy-1-hydroxy-2,2,6,6-tetramethylpiperidine with acrylamide is reported by T. Miyazawa et al, Synthesis, 1984, 1034. No utility is given for the product obtained.

4-Benzoyloxy-1-oxyl-2,2,6,6-tetramethylpiperidine has been used to trap radicals generated from the decomposition of di-tert-butyl peroxalate and dibenzoyl peroxide in the presence of methyl crotonate, methyl methacrylate and methyl acrylate as reported by G. Moad et al, Aust. J. Chem. 36, 1573 (1983). The use of the products prepared as polymer light stabilizers is not disclosed or suggested.

The Michael addition products of N,N-dialkylhydroxylamines with vinylphosphonate esters are reported in U.S. Pat. No. 4,753,972. These amino-oxyethylphosphonates are color improvers and process stabilizers for polyolefins.

4-Hydroxy-1-oxyl-2,2,6,6-tetramethylpiperidine and 1-oxyl-2,2,6,6-tetramethylpiperidin-4-one have also been used to trap radicals formed from the addition of hydroxy radicals to the double bond in thymine and thymidine as reported by J. Cadet et al, Tetrahedron, 35, 2743 (1979); Inst. J. Radiat. Biol Rel Stud Phys., Chem. Med, 30, 1 (1976); by F. Hruska et al, Can J. Chem, 63, 15 (1985). The use of these products as polymer light stabilizers is not disclosed or suggested.

Some N-hydroxy hindered amines are described in U.S. Pat. Nos. 4,590,231; 4,649,221; 4,691,015; 4,668,721; and 4,703,073.

DETAILED DISCLOSURE

The instant compounds are the Michael addition products having one of formulas I to VIII wherein $G_1$ and $G_2$ are independently alkyl of 1 to 4 carbon atoms, or $G_1$ and $G_2$ together are pentamethylene, $R_1$ is hydrogen, methyl or phenyl, $R_2$ is hydrogen or methyl, $R_3$ is hydrogen or alkyl of 1 to 4 carbon atoms, X is alkoxy of 1 to 18 carbon atoms, $-NH_2$, $-NHR_6$, $-N(R_6)_2$ or a radical selected from the group consisting of -continued

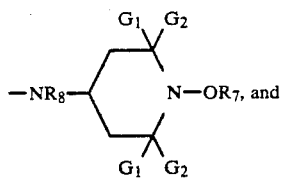

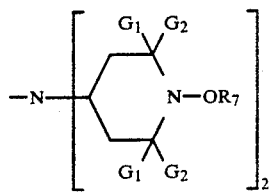

where

R₆ is alkyl of 1 to 8 carbon atoms, or phenyl,

R₇ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, R₈ is hydrogen or alkyl of 1 to 8 carbon atoms, R₄ is hydrogen or methyl, R₅ is hydrogen or methyl, Y is —O—, —NH—, —NR₉— or

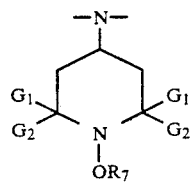

where R₉ is alkyl of 1 to 18 carbon atoms,

Z is —NH—CO—NH— or —CH₂C(CH₃)₂CH₂—,

L is —O—R₁₀—O—,

—NH—R₁₀—NH—, —NR₈—R₁₀—NR₈— or

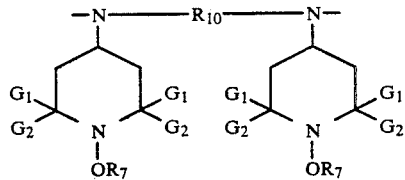

where

R₁₀ is alkylene of 2 to 18 carbon atoms or arylene of 6 to 10 carbon atoms,

G is alkylene of 1 to 12 carbon atoms or arylene of 6 to 10 carbon atoms,

T is an n-valent radical selected from the group consisting of a carboxyl radical of an aliphatic, cycloaliphatic or aromatic acid, hydroxy, alkoxy, cycloalkoxy, aralkoxy, an aminyl radical of an aliphatic or aromatic primary or secondary amine or of melamine or of an N-substituted melamine, an amidyl radical of an aliphatic or aromatic amide, carbamide or carbamate and an imidyl radical of a saturated imide, or T is a 2n-valent alkoxy diradical forming a 1,3-dioxolane or 1,3-dioxane ring, or T is a divalent radical of hydantoin or N-substituted hydantoin or a divalent carbon radical of 2,2-substituted 4-oxazolidone, E has the same definitions as T, and n is an integer from 1 to 4, with the proviso that in formula I when n is 1, T is benzyloxy and R₁, R₂ and R₃ are each hydrogen, X is not —NH₂; that in formula I, when n is 1, T is benzoyloxy and R₁, R₂ and R₃ are each hydrogen, X is not methoxy; that in formula I, when n is 1, T is benzoyloxy, X is methoxy and R₃ is hydrogen, R₁ or R₂ is not methyl when the other of R₁ or R₂ is hydrogen.

Preferably G₁ and G₂ are each methyl.

Preferably R₁ is hydrogen or methyl, most preferably hydrogen.

Preferably R₂ is hydrogen.

Preferably X is alkoxy of 1 to 12 carbon atoms or is

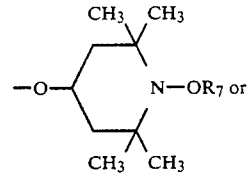

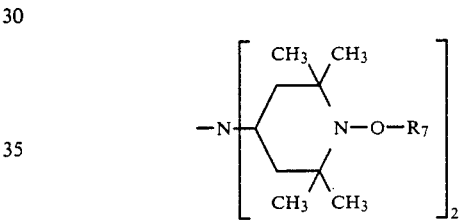

where R₇ is alkyl of 1 to 12 carbon atoms or cyclohexyl, most preferably methyl, heptyl, octyl, nonyl or cyclohexyl.

Preferably R₈ is hydrogen.

Preferably R₄ and R₅ are each hydrogen.

Preferably Y is

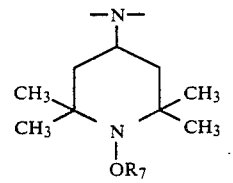

where R₇ is preferably defined above.

Preferably Z is —NHCONH—,

Preferably L is —O—R₁₀—O— where R₁₀ is alkylene of 2 to 12 carbon atoms, most preferably ethylene, tetramethylene and 2,2-dimethyltrimethylene.

Preferably G is o-phenylene, m-phenylene or p-phenylene.

Preferably n is 1 or 2.

Preferably the compound is of formula I.

The instant compounds are prepared by the reaction of an N-hydroxy hindered amine with a whole array of alpha,beta-unsaturated carbonyl compounds.

Hydroxylamines are conveniently prepared by the oxidation of amines to the N-oxyl intermediates using hydrogen peroxide as taught by E. G. Rozantsev et al, Synthesis, 1971, 190; or by an organic hydroperoxide and metal oxide catalyst followed by catalytic hydrogenation (U.S. Pat. No. 4,665,185).

The N-hydrocarbyloxy hindered amines are prepared by several routes. N-Methoxy derivatives are prepared by reaction of an N-oxyl compound with methyl radicals generated from the thermolysis of di-tert-butyl peroxide in an inert solvent such as chlorobenzene.

N-Hydroxy derivatives can be alkylated by reaction with sodium hydride and an alkyl halide. A preferred method for preparing N-hydrocarbyloxy compounds involves the thermal reaction of a hydrocarbon solution of a hindered amine or its N-oxyl derivative with tert-butyl hydroperoxide and a metal oxide catalyst as taught in copending patent application Ser. No. 259,949 now abandoned.

The alpha,beta-unsaturated carbonyl intermediates are largely items of commerce or can be prepared by conventional methods starting from 4-amino- and 4-hydroxy-substituted hindered amines.

Typical alpha,beta-unsaturated carbonyl intermediates are the esters, amides, acids, imides and ketones typified by the acrylates, methacrylates, cinnamates, tiglates, crotonates, itaconates, citraconates, senecioates (=dimethylacrylates), phorone, isophorone, maleates, fumarates, maleimides, uracils and the like.

Another aspect of the instant invention pertains to compounds which are the Michael addition products having formula IX, and to polymer compositions stabilized therewith,

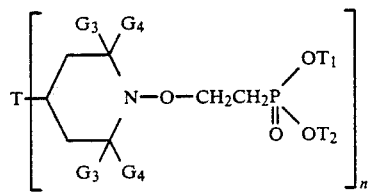

(IX)

wherein

T is defined as described above, n is 1 to 4, $G_3$ and $G_4$ are independently alkyl of 1 to 4 carbon atoms, or $G_3$ and $G_4$ together are pentamethylene, and $T_1$ and $T_2$ are independently hydrogen, alkyl of 1 to 36 carbon atoms, cycloalkyl of 5 to 12 carbon atoms, aralkyl of 7 to 9 carbon atoms or said aralkyl substituted by alkyl of 1 to 36 carbon atoms, or the alkali metal or alkaline earth metal salts thereof.

Preferably T is monovalent and n is 1.

Preferably $G_3$ and $G_4$ are each methyl.

Preferably $T_1$ and $T_2$ are independently alkyl of 1 to 18 carbon atoms, cyclopentyl, cyclohexyl, benzyl, alpha-methylbenzyl or alpha,alpha-dimethylbenzyl.

Most preferably $T_1$ and $T_2$ are alkyl of 1 to 8 carbon atoms, especially ethyl.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety

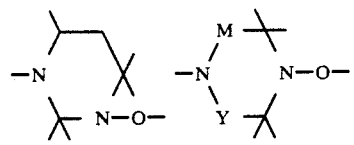

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene 4. Polystyrene, poly-(p-methylstyrene).

5. Copolymers of styrene or methylstyrene with dienes or acrylic derivatives, such as, for example, styrene /butadiene, styrene/acrylonitrile, styrene /ethyl methacrylate , styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates, on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers 7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14 Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as blockcopolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone -acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)

2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5di-tert-butyl-4-hydroxyphenylpropionyl)-hydrazine

2. UV absorbers and light stabilizers 1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ester or isooctyl ester, α-carbomethoxy-cinnamic acid methyl ester, α-cyano-β-methyl-p-methoxycinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyl-oxanilide, 2,2'-di-dodecyloxy-5,5'-di-tert-butyl-oxanilide, 2-ethoxy2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy4-(2-hydroxyethoxy)-phenyl]-6-(2,4-dimethylphenyl)-s-triazine; 2,4-bis[2-hydroxy-4-(2-hydroxyethoxy)phenyl]-6-(4-bromo-phenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, L N,N'-bis-salicyloylhydrazine, N,N'-bis-(3,5-di-tert-butyl4-hydroxyphenylpropionyl)-hydrazine, 3-salicyloylamino1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-ditertbutylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example,.esters of β-thiodipropionic acid, for example the lauryl, stearyl, myristyl or tridecyl esters, mercaptobenzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flame-proofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines: and epoxy resins crosslinked with carboxylic acids, anhydrides, polyamines or mercaptans: and acrylic and polyester-resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229–238, and in S. Paul's "Surface Coatings Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes Of UV absorbers which may be used in the instant compositions in conjunction with the aforementioned piperidine compounds are referenced in a paper by H. J. Heller in European Polymer Journal Supplement, 1969, pp 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorvers of especial importance are:

(a) 2-(2'-Hydroxyphenyl)-benzotriazoles, for example , the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tertbutyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-$\beta,\beta$-diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octylide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyloxanilide and its mixtures of ortho- and para-methoxy- as well as of o- and p-ethoxy-disubstituted oxanilides (f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alphadimethyl-benzyl)phenyl]-2H-benzotriazole, dodecylated 2-(2-hydroxy-5-methylphenyl)-2H-benzotriazole, 2-[2-hydroxy-3-tert-butyl-4-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylpheny]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising (a) an acid catalyze d thermoset coating or enamel based on hot crosslinkable acrylic, polyester or alkyd resins, (b) a NO-substituted 2,2,6,6-tetraalkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite , tris-(2,4-di-tert.butylphenyl) phosphite, diisodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1

4-Benzyloxy-1-[2-(methoxycarbonyl)ethoxy]-2,2,6,6-tetramethylpiperidine

A mixture of 20.0 grams (76 mmol) of 4-benzyloxyl-oxyl-2,2,6,6-tetramethylpiperidine, 10.0 grams of anhydrous magnesium sulfate, 500 mg of 5% palladium on carbon and 150 ml of tetrahydrofuran is hydrogenated on a Parr apparatus (50 psi, ambient temperature). Catalyst and drying agent are removed by filtration and the filtrate is quickly transferred to a flask under a nitrogen atmosphere. To the flask are added 0.85 gram of potassium tert-butoxide, 19.7 grams (229 mmol) of methyl acrylate, and 50 ml of tetrahydrofuran. The reaction mixture is stirred at ambient temperature for three hours and at 55° C. for one hour. The reaction mixture is partitioned between ether (300 ml) and saturated sodium bicarbonate solution (150 ml). The ether layer is washed with water (2×500 ml), washed with saturated aqueous sodium chloride (200 ml), dried over anhydrous magnesium sulfate and concentrated to an oil. The oil is purified by flash chromatography (silica gel; 9:1 hexane:ethyl acetate) to afford 13.0 grams of the title compound as a colorless liquid.

Analysis: Calcd for $C_{20}H_{31}NO_4$: C, 68.7; H, 8.9; N, 4.0; Found: C, 69.6; H, 8.9; N, 4.1.

EXAMPLE 2 alpha,alpha'-Bis[1-(2-methoxycarbonylethoxy)-2,2,6,6-tetramethylpiperidin-4-yloxy]-p-xylene Methyl acrylate (64.9 grams, 750 mmol) is rapidly added under a nitrogen atmosphere to a mixture of 16.9 grams (38 mmol) of alpha,alpha'-bis(1-hydroxy-2,2,6,6-tetramethylpiperidin-4-yloxy)-p-xylene, 0.85 gram of potassium tert-butoxide and 70 ml of tetrahydrofuran. The reaction is exothermic and the temperature exceeds 40° C. for one hour. The reaction mixture is then heated at 60° C. for four hours and allowed to stand overnight at ambient temperature. The reaction mixture is diluted with ether (300 ml), washed consecutively with saturated sodium bicarbonate solution (200 ml), water (4×500 ml), and saturated sodium chloride solution (200 ml), dried over anhydrous magnesium sulfate and evaporated to an oil. The oil is stirred with methanol and a precipitate forms. The supernatant liquid is concentrated to give a solid which is purified by flash chromatography (silica gel; 9:1 hexane:ethyl acetate) to afford 4.6 grams (20% yield) of the title compound as a white solid melting at 84°-85° C.

Analysis: Calcd for $C_{34}H_{56}N_2O_8$: C, 65.8; H, 9.1; N, 4.5; Found: C, 65.4; H, 9.0; N, 4.7.

EXAMPLE 3

Bis[1-(2-methoxycarbonylethoxy)-2,2,6,6-tetramethylpiperidin-4-yl] Phthalate

A mixture of 25.0 grams (52.7 mmol) of bis(1-oxyl-2,2,6,6-tetramethylpiperidin-4-yl) phthalate, 10.0 grams of magnesium sulfate, 100 mg of 5% palladium on carbon, and 200 ml of tetrahydrofuran is hydrogenated (50 psi, ambient temperature) on a Parr apparatus. Solids are removed by filtration. The filtrate is cooled to 10° C. (under nitrogen atmosphere) and treated with 0.6 gram (5.3 mmol) of potassium tert-butoxide. Methyl acrylate (45.5 grams, 527 mmol) is added to the reaction mixture over a five-minute period. The reaction mixture is then stirred at ambient temperature for two hours, treated with another portion of 0.6 gram of potassium tert-butoxide and stirred overnight at ambient temperature. The reactions mixture is diluted with ether (300 ml), washed with 1N hydrochloric acid (2×200 ml), washed with saturated sodium bicarbonate solution (200 ml), dried over anhydrous magnesium sulfite and concentrated to an oil. The oil is purified by flash chromatography (silica gel; 4:1 hexane: ethyl acetate) to yield a solid which is recrystallized from methanol to afford 8.8 grams (26% yield) of the title compound as a white solid melting at 117°–118° C.

Analysis: Calcd for $C_{34}H_{52}N_2O_{10}$: C, 62.9; H, 8.1; N, 4.3; Found: C, 63.0; H, 8.2; N, 4.2.

EXAMPLE 4

Bis[1-(2-methoxycarbonylethoxy)-2,2,6,6-tetramethylpiperidin-4-yl] Isophthalate

When following the general procedure of Example 3 an equivalent amount of bis(1-oxyl-2,2,6,6-tetramethylpiperidin-4-yl) isophthalate is substituted for bis(1-oxyl-2,2,6,6-tetramethylpiperidin-4-yl) phthalate, the title compound is obtained as a white solid melting at 94°–96° C.

Analysis: Calcd for $C_{34}H_{52}N_2O_{10}$: C, 62.9; H, 8.1; N, 4.3; Found: C, 62.9; H, 7.9; N, 4.6.

EXAMPLE 5

4-Benzoyloxy-1-(2-methoxycarbonylethoxy)-2,2,6,6-tetramethylpiperidine

When following the general procedure of Example 3 the bis(1-oxyl-2,2,6,6-tetramethylpiperidin-4-yl) phthalate is replaced by an equivalent amount of 4-benzoyloxy-1-oxyl-2,2,6,6-tetramethylpiperidine, the title compound is obtained as a white solid melting at 64°–69° C.

Analysis: Calcd for $C_{20}H_{29}NO_5$: C, 66.1; H, 8.0; N, 3.9; Found: C, 66.3; H, 8.0; N, 4.0.

EXAMPLE 6

4-Benzoyloxy-1-(1-phenylsuccinimid-3-yloxy-2,2,6,6-tetramethylpiperidine

A mixture of 5.5 grams (19.8 mmol) of benzoyloxy-1-hydroxy-2,2,6,6-tetramethylpiperidine, 3.5 grams (20.0 mmol) of N-phenylmaleimide and 40 ml of tetrahydrofuran is stirred for several minutes and the stoppered and allowed to stand at 25° C. for 64 hours. Solvent is then evaporated and the residue is recrystallized from methanol to afford 1.7 grams (19% yield) of the title compound as a white crystalline solid melting at 135°–136° C.

Analysis: Calcd for $C_{26}H_{30}N_2O_5$: C, 69.3; H, 6.7; N, 6.2; Found: C, 69.3; H, 6.8; N, 6.3.

EXAMPLE 7

1,4-Butanediyl Bis[3-(-octadecanoyloxy-2,2,6,6-tetramethylpiperidin-1-yloxy)propionate]

The title compound is prepared from 1,4-butanediyl diacrylate and 1-hydroxy-4-octadecanoyloxy-2,2,6,6-tetramethylpiperidine according to the general procedure of Example 2.

EXAMPLE 8

Bis(1-[2-(1-cyclohexyloxy-2,2,6,6-tetramethylpiperidin-4-yl oxy)-carbonylethoxy]-2,2,6,6-tetramethylpiperidin-4-yl) Sebacate The title compound is prepared from 1-cyclohexyloxy-2,2,6,6-tetramethylpiperidin-4-yl acrylate and bis(1-hydroxy-2,2,6,6-tetramethylpiperidin-4-yl) sebacate according to the general procedure of Example 2.

EXAMPLE 9

Bis(1-[2-(1-methoxy-2,2,6,6-tetramethylpiperidin-4-yloxycarbonyl)ethoxy]-2,2,6,6-tetramethylpiperidin-4-yl) Sebacate The title compound is prepared from 1-methoxy-2,2,6,6-tetramethylpiperidin-4-yl acrylate and bis(1-hydroxy-2,2,6,6-tetramethylpiperidin-4-yl) sebacate according to the general procedure of Example 2.

EXAMPLE 10

Bis(1-[2-(1-octadecyloxy-2,2,6,6-tetramethylpiperidin-4yloxycarbonyl)ethoxy]-2,2,6,6-tetramethylpiperidin-4-yl) Sebacate The title compound is prepared from 1-octadecyloxy-2,2,6,6-tetramethylpiperidin-4-yl acrylate and bis(1-hydroxy-2,2,6,6-tetramethylpiperidin-4-yl) sebacate according to the general procedure of Example 2.

EXAMPLE 11

4-Benzoyloxy-1-[2-[2-(1-cyclohexyloxy-2,2,6,6-tetramethylpiperidin-4-yloxycarbonyl)ethoxy]-2,2,6,6-tetramethylpiperidine A mixture of 11.3 grams (40.7 mmol) of 4-benzoyloxy-1-hydroxy-2,2,6,6-tetramethylpiperidine, 12.0 grams (38.8 mmol) of 1-cyclohexyloxy-2,2,6,6-tetramethylpiperidin-4-yl acrylate, 0.21 gram of potassium tert-butoxide and 50 ml of tetrahydrofuran is stirred for 30 minutes and then stoppered and allowed to stand for 72 hours at room temperature. The reaction mixture is then purified by flash chromatography on silica gel (4:1, heptane: ethyl acetate) to obtain 8.2 grams (36% yield) of the title compound as a colorless glass.

Analysis: Calcd for $C_{34}H_{54}N_2O$: C, 69.6; H, 9.3; N, 4.8; Found: C, 68.8; H, 9.6; N, 4.6.

EXAMPLE 12

4-Benzoyloxy-1-[2-(1-octyloxy-2,2,6,6-tetramethylpiperidin-4-oxycarbonyl)ethoxy]-2,2,6,6-tetramethylpiperidine A mixture of 19.2 grams (69.6 mmol) of 4-benzoyloxy-1-oxyl-2,2,6,6-tetramethylpiperidine, 0.8 grams of 10% palladium on carbon, 2.0 grams of anhydrous magnesium sulfate and 100 ml of anhydrous tetrahydrofuran is hydrogenated (48 psi, 25° C.) on a Parr apparatus for three hours. Solids are then removed by filtration. To the filtrate are added 19.7 grams (58.0 mmol) of 1-octyloxy-2,2,6,6-tetramethylpiperidin-4-yl acrylate, 0.8 gram of potassium tert-butoxide and 40 ml of tetrahydrofuran. The reaction mixture is purged with nitrogen, stoppered and allowed to stand at 25° C. for five days. The mixture is then diluted with diethyl ether (200 ml), and washed successively with 1N hydrochloric acid (2×75 ml) and saturated sodium bicarbonate solution (200) ml), and then dried over anhydrous magnesium sulfate and concentrated to a pink residue. Purification by flash chromatography on silica gel (4:1, heptane:ethyl acetate) affords 12.7 grams (35% yield) of the title compound as a colorless syrup.

Analysis: Calcd for $C_{36}H_{60}N_2O_6$: C, 70.1; H, 9.8; N, 4.5; Found: C, 70.3; H, 10.2; N, 4.8.

EXAMPLE 13

4-Benzoyloxy-1-[2-(1-methoxy-2,2,6,6-tetramethyl-piperidin-4-yloxycarbonyl)ethoxy]-2,2,6,6-tetramethyl-piperidine The title compound is prepared in 50% yield as a colorless syrup from 4-benzoyloxy-1-oxyl-2,2,6,6-tetramethylpiperidine and 1-methoxy-2,2,6,6-tetramethylpiperidin-4-yl acrylate following the general procedure of Example 12.

Analysis: Calcd for $C_{29}H_{46}N_2O_6$: C, 67.1; H, 8.9; N, 5.4; Found: C, 67.1; H, 9.2; N, 5.2.

EXAMPLE 14

Bis[1-(2-[1-methoxy-2,2,6,6-tetramethylpiperidin-4-yloxycarbonyl]-ethoxy)-2,2,6,6-tetramethylpiperidin-4-yl] Isophthalate The title compound is prepared in a 31% yield as a colorless glass from bis(1-oxyl-2,2,6,6-tetramethylpiperidin-4-yl) isophthalate and 1-methoxy-2,2,6,6-tetramethylpiperidin-4-yl acrylate according to the general procedure of Example 12. The reaction is reduced from five days to 48 hours in this case.

Analysis: Calcd for $C_{52}H_{86}N_4O_{12}$: C, 65.1; H, 9.6; N, 5.8; Found: C, 64.5; H, 9.4; N, 5.6.

EXAMPLE 15

1,2-Bis[3-(4-benzoyloxy-2,2,6,6-tetramethylpiperidin-1-yloxy)-succinimido]benzene The title compound is prepared from N,N'-1,2-phenylenedimaleimide and 4-benzoyloxy-1-hydroxy-2,2,6,6-tetramethylpiperidine according to the general procedure of Example 6.

EXAMPLE 16

Bis[1-(1-phenylsuccinimid-3-yloxy)-2,2,6,6-tetramethyl-piperidin-4-yl] Sebacate

A mixture of 10.0 grams (19.6 mmol) of bis(1-oxyl-2,2,6,6-tetramethylpiperidin-4-yl) sebacate, 0.2 gram of 10% palladium on carbon and 50 ml of tetrahydrofuran is hydrogenated (50 psi, 25° C.) on a Parr apparatus for three hours. Solids are then removed by filtration and to the filtrate are added 6.8 grams (19.6 mmol) of N-phenylmaleimide and 10 ml of tetrahydrofuran. The reaction mixture is purged with nitrogen, stoppered and allowed to stand at room temperature for nine days. Solvent is then evaporated and the residue is purified by flash chromatography on silica gel (2:1, heptane:ethyl acetate). Recrystallization of the crude product from 2:1 heptane:ethyl acetate afford 2.2 grams (13% yield) of the title compound as a white solid melting at 102°-108° C. Solvent is then evaporated and the residue is purified by flash chromatography on silica gel (2:1, heptane:ethyl acetate). Recrystallization of the crude product from 2:1 heptane:ethyl acetate afford 2.2 grams (13% yield) of the title compound as a white solid melting at 102°-108° C.

Analysis: Calcd for $C_{48}H_{66}N_4O_{10}$: C, 67.1; H, 7.7; N, 6.5; Found: C, 67.1; H, 7.9; N, 6.3.

EXAMPLE 17

Light Stabilization of Polypropylene

This example illustrates the light stabilizing effectiveness of instant stabilizers.

Polypropylene powder (Hercules Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
|---|---|---|
| Base Resin | — | 340 |
| Example 4 | 0.1 | 1290 |
| Example 5 | 0.1 | 760 |

EXAMPLE 18

Stabilization of High Solids Thermoset Acrylic Resin Enamel

A thermoset acrylic enamel based on a binder of 70% of monomers such as hydroxyethyl acrylate, butyl acrylate, methylmethacrylate, styrene and acrylic acid with 30% of a melamine resin and an acid catalyst, such as p-toluenesulfonic acid, dinonylnaphthalene disulfonic acid or dodecylbenzenesulfonic acid is formulated to include a benzotriazole UV absorber and a hindered amine light stabilizer.

Commercially available epoxy primed 4" × 12" panels (Uniprime from Advanced Coatings Technology) are spray coated with a silver metallic basecoat to a thickeness of about 0.8 mil (0.023 mm) and air dried for 3 minutes. The stabilized thermoset acrylic resin enamel is then sprayed onto the basecoated panel to a thickness of about 1.7 mil. After 15 minutes air-drying, the coated sheets are baked for 30 minutes at 250° F. (121° C.).

After storage for 1 week in an air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV and the time to cracking of the clearcoat is determined.

| Additives in Clearcoat (% by wt) | Time to Cracking (hr) |
|---|---|
| Unstabilized | 950 |
| 3.5% UVA | 1450 |
| 3.5% UVA + 1.5% Compound of Example 1 | 2900 |
| Unstabilized | 1200 |
| 3.5% UVA + 1.5% Compound of Example 2 | 4800 |

*UVA is 2-[2-hydroxy-3-tert-butyl-5-(2-(omega-hydroxy-octa-(ethyleneoxy)carbonyl)-ethylphenyl]-2H-benzotriazole

EXAMPLE 19

The thermoset acrylic enamel of Example 18 is formulated to include a benzotriazole UV absorber and various hindered amines of the invention. The silver metallic basecoat is stabilized with 3% UVA (based on resin solids) prior to application. The enamel is coated over the basecoat pursuant to the procedure in Example 18 and baking is conducted for 30 minutes at 121° C.

The coated panels are exposed in the QUV exposure apparatus and the time to cracking of the coating is determined.

| Compound (% by wt) | Time to Cracking (hr) |
|---|---|
| Unstabilized* | 1200 |
| 3% UVA** | 2250 |
| 3% UVA + 1% Compound of Example 3 | 4500 |
| 3% UVA + 1% Compound of Example 4 | 4800 |

*No additive in either basecoat or clearcoat.
**UVA is named in Example 18.

EXAMPLE 20

Stabilization of a Thermoplastic Acrylic Lacquer

A commercially available light blue metallic thermoplastic acrylic lacquer is used. This material is stabilized with the indicated amounts of UVA+HALS (by weight on total resin solids) then spray applied onto Bonderite 40 panels primed with an epoxy primer. After storage at ambient temperature for 2 weeks, the panels are exposed in a Xenon Arc Weatherometer for 1250 hours. The 60° gloss values of the panels are reported in Table 1.

TABLE 1

| Additive* | 60° Gloss |
|---|---|
| 2% UVA 2 + 2% Compound of Example 1 | 27 |
| 2% UVA 2 + 2% Compound of Example 3 | 24 |
| 2% UVA 2 + 2% Compound of Example 4 | 28 |

*UVA 2 is 2-[2-hydroxy-3,5-(alpha,alpha-dimethylbenzyl)-phenyl]-2H-benzotriazole.

EXAMPLE 21

Stabilization of an Medium Oil Alkyd Enamel

A commercially available medium oil alkyd enamel pigmented with non-leafing aluminum pigment and tinted light blue is used. This material is stabilized with the indicated amounts of UVA+HALS (% by weight) then spray applied onto cold rolled steel panels primed with an epoxy primer. After the coating is allowed to cure at room temperature for 2 weeks, the panels are exposed in a Xenon Arc Weatherometer for 840 hours. The 20° gloss retention of the panels is reported in Table 2.

TABLE 2

| Additive | % 20° Gloss Retention |
|---|---|
| 3% UVA* + 2% Compound of Example 1 | 30.3 |

*UVA named in Example 18

EXAMPLE 22

Stabilization of an Acrylic Alkyd Refinish Enamel

A commercially available acrylic alkyl enamel pigmented with non-leafing aluminum pigment and tinted a light blue is used. This material is stabilized with the indicated amounts of UVA+HALS (% by weight on dry resin) then spray applied onto Bonderite 40 panels primed with an alkyd primer. After the coating is allowed to cure at room temperatures for 14 days, the panels are exposed outdoors at an angle of 5° south for a period of 8 months. The 20° gloss of the panels were measured and are reported in Table 3.

TABLE 3

| Additive* | 20° Gloss |
|---|---|
| 3% UVA + 2% Compound of Example 1 | 32 |
| 3% UVA + 2% Compound of Example 3 | 32 |
| 3% UVA + 2% Compound of Example 4 | 36 |

*UVA is named in Example 18

EXAMPLE 23

Stabilization of an Acrylic Alkyd Crosslinked with an Aliphatic Isocyanate Refinish Enamel A commercially available silver metallic acrylic alkyd enamel hardened with an aliphatic isocyanate is used. This material is stabilized with the indicated amounts of UVA+HALS (% by weight on total resin solids), then spray applied onto Bonderite 40 panels primed with a black alkyl primer. After the coatings are aged at ambient temperature for 2 weeks the panels are exposed outdoors at an angle of 5° south for a period of 21 months. The 20° gloss of the panels are reported in Table 4.

TABLE 4

| Additive | 20° Gloss |
|---|---|
| 3% UVA* + 2% Compound of Example 3 | 27 |

*UVA named in Example 15

EXAMPLE 24

Stabilization of an Acrylic Urethane Enamel

A two-component acrylic urethane enamel is stabilized with the indicated amounts of ultraviolet light absorber and hindered amine light stabilizer.

Cold rolled steel panels (4"×12" Bonderite 40) are coated with a commercial epoxy polyamide refinish primer at a dry film thickness of about 1 mil. The primed panels are stored for 1-2 days at ambient temperatures and are then coated with about 0.8 mil of a thermoplastic acrylic silver metallic basecoat. The basecoated panels are air dried for 30-40 minutes and are then topcoated with about 2.2 mils of the stabilized enamels. After ambient storage for 1 week, the panels are exposed for accelerated weathering in a Xenon Arc Weatherometer. The 20° gloss values of the panels are determined during exposure.

| Additive | 20° Gloss After Xenon Arc Exposure | | | | | | | |
|---|---|---|---|---|---|---|---|---|
| | 0 | 711 | 1303 | 1955 | 2256 | 2941 | 3238 | hrs. |
| Unstabilized | 83 | 77 | 67 | 60 | 12* | | | |
| 1.5% UVA** + 1.5% compound of Example 3 | 83 | 82 | 79 | 80 | 70 | 65 | 60 | |

*Clearcoat cracking is observed.
**UVA is named in Example 18

EXAMPLE 25

Diethyl 2-(4-Benzoyloxy-2,2,6,6-tetramethylpiperidin-1-oxy)ethylphosphonate

To a suspension of 0.12 gram of potassium tert-butoxide in 25 ml of dry tetrahydrofuran is added 3.0 grams of 4-benzoyloxy-1-hydroxy-2,2,6,6-tetramethylpiperidine. After stirring the solution under nitrogen at room temperature for ten minutes, 1.78 grams of diethyl vinylphosphonate are added. After stirring the reaction mixture at room temperature under nitrogen for 24 hours, the solvent is removed under reduced pressure. The residue is partitioned between water and methylene chloride. The organic phase is washed with water, then brine and finally dried over anhydrous magnesium sulfate followed by evaportion. Purification of the residue by liquid chromatography affords the title compound as a colorless liquid. Analysis by nmr, ir and ms gives data consistent with the structure of the title compound.

What is claimed is:

1. A compound having one of the formulas I to VIII

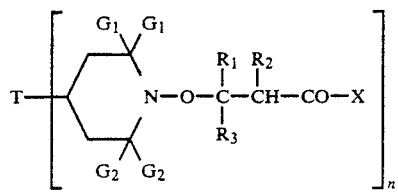 (I)

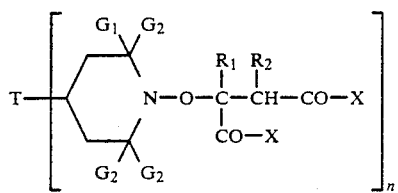 (II)

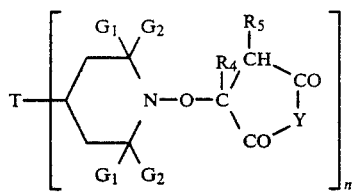 (III)

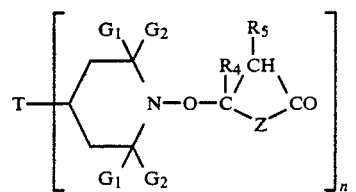 (IV)

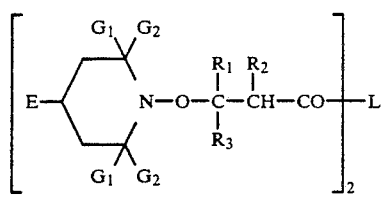 (V)

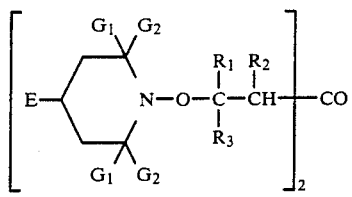 (VI)

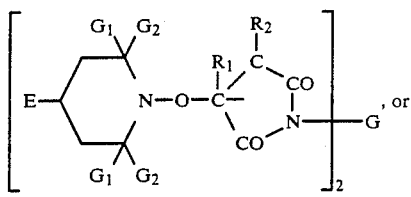 (VII)

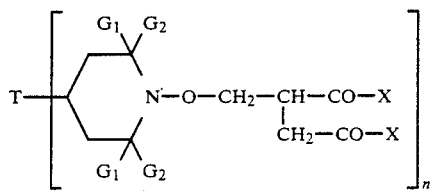 (VIII)

wherein
$G_1$ and $G_2$ are independently alkyl of 1 to 4 carbon atoms, or $G_1$ and $G_2$ together are pentamethylene,
$R_1$ is hydrogen, methyl or phenyl,
$R_2$ is hydrogen or methyl,
$R_3$ is hydrogen or alkyl of 1 to 4 carbon atoms,
X is alkoxy of 1 to 18 carbon atoms, $-NH_2$, $-NHR_6$, $-N(R_6)_2$ or a radical selected from the group consisting of

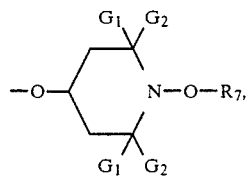

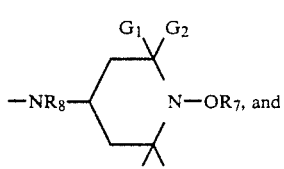

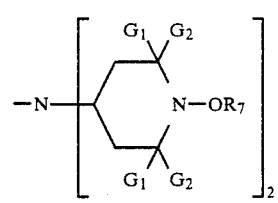

where
$R_6$ is alkyl of 1 to 8 carbon atoms, or phenyl,
$R_7$ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, $R_8$ is hydrogen or alkyl of 1 to 8 carbon atoms,
$R_4$ is hydrogen or methyl,
$R_5$ is hydrogen or methyl,
Y is —O—, —NH—, —NR$_9$— or

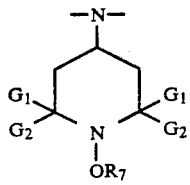

where $R_9$ is alkyl of 1 to 18 carbon atoms,
Z is —NH—CO—NH— or
—CH$_2$C(CH$_3$)$_2$CH$_2$—,

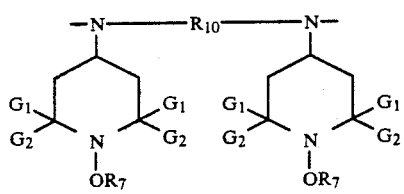

where
$R_{10}$ is alkylene of 2 to 18 carbon atoms or arylene of 10 carbon atoms, G is alkylene of 1 to 12 carbon atoms or arylene of 6 to 10 carbon atoms, T is an n-valent radical selected from the group consisting of a carboxyl radical of an aliphatic, cycloaliphatic or aromatic acid, hydroxy, alkoxy, cycloalkoxy, aralkoxy, an aminyl radical of an aliphatic or aromatic primary or secondary amine or of melamine or of an N-substituted melamine, an amidyl radical of an aliphatic or aromatic amide, carbamide or carbamate and an imidyl radical of a saturated imide, or T is a 2n-valent alkoxy diradical forming a 1,3-dioxolane or 1,3-dioxane ring, or T is a divalent radical of hydantoin or N-substituted hydantoin or a divalent carbon radical of 2,2-substituted 4-oxazolidone, E has the same definitions as T, and n is an integer from 1 to 4, with the proviso that in formula I when n is 1, T is benzyloxy and $R_1$, $R_2$ and $R_3$ are each hydrogen, X is not —NH$_2$; that in formula I, when n is 1, T is benzoyloxy and $R_1$, $R_2$ and $R_3$ are each hydrogen, X is not methoxy; that in formula I, when n is 1, T is benzoyloxy, X is methoxy and $R_3$ is hydrogen, $R_1$ or $R_2$ is not methyl when the other of $R_1$ and $R_2$ is hydrogen.

2. A compound according to claim 1 where $G_1$ and $G_2$ are each methyl.

3. A compound according to claim 1 wherein $R_1$ is hydrogen or methyl.

4. A compound according to claim 3 wherein $R_1$ is hydrogen.

5. A compound according to claim 1 wherein $R_2$ is hydrogen.

6. A compound according to claim 1 wherein X is alkoxy of 1 to 12 carbon atoms or is

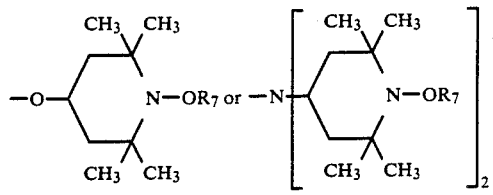

where $R_7$ is alkyl of 1 to 12 carbon atoms or cyclohexyl.

7. A compound according to claim 6 wherein $R_7$ is methyl, heptyl, octyl, nonyl or cyclohexyl.

8. A compound according to claim 1 wherein $R_8$ is hydrogen.

9. A compound according to claim 1 wherein $R_4$ and $R_5$ are each hydrogen.

10. A compound according to claim 1 wherein Y is

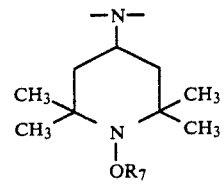

where $R_7$ is alkyl of 1 to 12 carbon atoms or cyclohexyl.

11. A compound according to claim 1 wherein Z is —NHCONH—.

12. A compound according to claim 1 wherein L is —O—R$_{10}$—O— where $R_{10}$ is alkylene of 2 to 12 carbon atoms.

13. A compound according to claim 12 wherein $R_{10}$ is ethylene, tetramethylene or 2,2-dimethyltrimethylene.

14. A compound according to claim 1 wherein G is o-phenylene, m-phenylene or p-phenylene.

15. A compound according to claim 1 wherein n is 1 or 2.

16. A compound according to claim 1 having formula I.

17. The compound according to claim 1 which is 4-benzyloxy-1-(2-methoxycarbonylethoxy)-2,2,6,6-tetramethylpiperidine.

18. The compound according to claim 1 which is alpha,alpha'-bis[1-(2-methoxycarbonylethoxy)-2,2,6,6-tetramethylpiperidin-4-yloxy]-p-xylene.

19. The compound according to claim 1 which is bis[1-(2-methoxycarbonylethyl)-2,2,6,6-tetramethylpiperidin-4-yl]phthalate.

20. The compound according to claim 1 which is bis[1-(2-methoxycarbonylethoxy)-2,2,6,6-tetramethylpiperidin-4-yl]isophthalate.

21. The compound according to claim 1 which is 4-benzoyloxy-1-[2-(1-cyclohexyloxy-2,2,6,6-tetramethylpiperidin-4-yloxycarbonyl)ethoxy]-2,2,6,6-tetramethylpiperidine;

4-benzoyloxy-1-[2-(1-octyloxy-2,2,6,6-tetramethylpiperidin-4-yloxycarbonyl)ethoxy]-2,2,6,6-tetramethylpiperidine;

4-benzoyloxy-1-[2-(1-methoxy-2,2,6,6-tetramethylpiperdin-4-yloxycarbonyl)ethoxy]-2,2,6,6-tetramethylpiperidine;

bis[1-(2-[1-methoxy-2,2,6,6-tetramethylpiperidin4-yloxycarbonylethoxy)-2,2,6,6-tetramethylpiperidin-4-yl]-isophthalate;

4-benzoyloxy-1-(1-phenylsuccinimid-3-yloxy)-2,2,6,6-tetramethylpiperidine; or bis [1-(1-phenylsuccinimid-3-yloxy)-2,2,6,6-tetramethylpiperidin-4-yl] sebacate.

22. A composition stabilized against the deleterious effects of actinic light which comprises
   (a) a synthetic polymer, and
   (b) a stabilizing amount of a compound having one of the formulas I to VIII

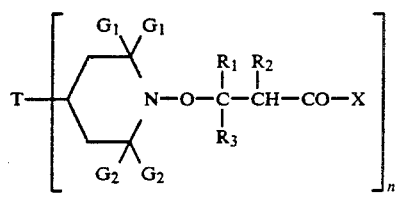 (I)

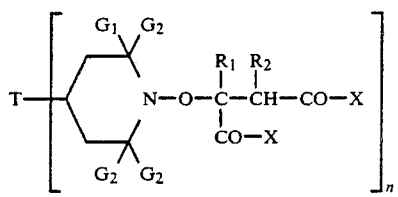 (II)

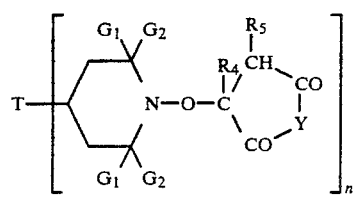 (III)

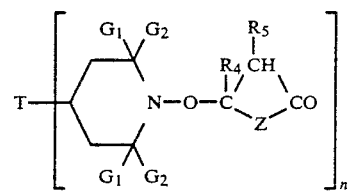 (IV)

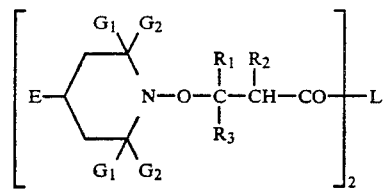 (V)

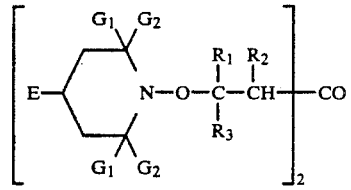 (VI)

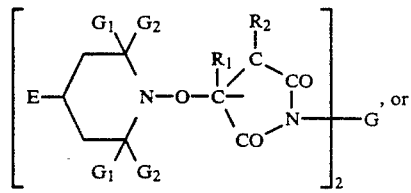 (VII)

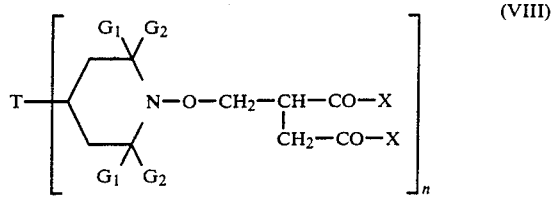 (VIII)

wherein
$G_1$ and $G_2$ are independently alkyl of 1 to 4 carbon atoms, or $G_1$ and $G_2$ together are pentamethylene,
$R_1$ is hydrogen, methyl or phenyl,
$R_2$ is hydrogen or methyl,
$R_3$ is hydrogen or alkyl of 1 to 4 carbon atoms,
X is alkoxy of 1 to 18 carbon atoms, —NH$_2$, —NHR$_6$, —N(R$_6$)$_2$ or a radical selected from the group consisting of

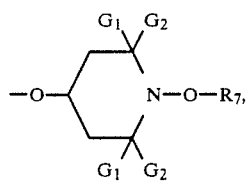

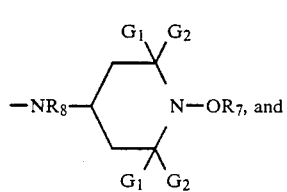

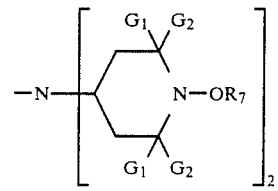

where
$R_6$ is alkyl of 1 to 8 carbon atoms, or phenyl,
$R_7$ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl,
$R_8$ is hydrogen or alkyl of 1 to 8 carbon atoms,
$R_4$ is hydrogen or methyl,
$R_5$ is hydrogen or methyl,
Y is —O—, —NH—, —NR$_9$—,

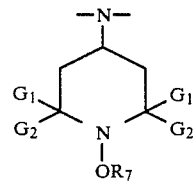

where $R_9$ is alkyl of 1 to 18 carbon atoms,

Z is —NH—CO—NH— or —CH$_2$C(CH$_3$)$_2$CH$_2$—,
L is —O—R$_{10}$—O—, —NH—R$_{10}$—NH—, —NR$_8$—R$_{10}$—NR$_8$— or

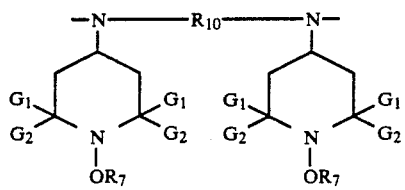

where
R$_{10}$ is alkylene of 2 to 18 carbon atoms or arylene of 6 to 10 carbon atoms,
G is alkylene of 1 to 12 carbon atoms or arylene of 6 to 10 carbon atoms,
T is an n-valent radical selected from the group consisting of a carboxyl radical of an aliphatic, cycloaliphatic or aromatic acid, hydroxy, alkoxy, cycloalkoxy, aralkoxy, an aminyl radical of an aliphatic or aromatic primary or secondary amine or of melamine or of an N-substituted melamine, an amidyl radical of an aliphatic or aromatic amide, carbamide or carbamate and an imidyl radical of a saturated or unsaturated imide, or
T is a 2n-valent alkoxy diradical forming a 1,3-dioxolane or 1,3-dioxane ring, or
T is a divalent radical of hydantoin or N-substituted hydantoin or a divalent carbon radical of 2,2-substituted 4-oxazolidone,
E has the same definitions as T, and
n is an integer from 1 to 4.

23. A composition according to claim 22 wherein the synthetic polymer is a polyolefin.

24. A composition according to claim 23 wherein the polyolefin is polypropylene.

25. A composition according to claim 22 wherein the compound of component (b) is bis[1-(2-methoxycarbonylethoxy)-2,2,6,6-tetramethylpiperidin-4-yl] isophthalate.

26. A composition according to claim 22 wherein the compound of component (b) is 4-benzoyloxy-1-(2-methoxycarbonylethoxy)-2,2,6,6-tetramethylpiperidine.

27. A composition according to claim 22 wherein the compound of component (b) is
4-benzyloxy-1-(2-methoxycarbonylethoxy)-2,2,6,6-tetramethylpiperidine;
alpha,alpha'-bis[1-(2-methoxycarbonylethoxy)-2,2,6,6-tetramethylpiperidin-4-yloxy]-p-xylene; or
bis[1-(2-methoxycarbonylethoxy)-2,2,6,6-tetramethylpiperidin-4-yl]phthalate.

28. A composition according to claim 22 wherein the polymer is a coating system based on alkyd, acrylic, acrylic-alkyd, polyester, epoxide, urethane, polyamide, vinyl or epoxy-polyester resins.

29. A composition according to claim 28 wherein the compound of component (b) is bis[1-(2-methoxycarbonylethoxy)-2,2,6,6-tetramethylpiperidin-4-yl] isophthalate.

30. A composition according to claim 28 wherein the compound of component (b) is 4-benzoyloxy-1-(3-methoxycarbonylethoxy)-2,2,6,6-tetramethylpiperidine.

31. A composition according to claim 28 wherein the compound of component (b) is
4-benzyloxy-1-(2-methoxycarbonylethoxy)-2,2,6,6-tetramethylpiperidine;
alpha,alpha'-b[1-(2-methoxycarbonylethoxy)-2,2,6,6-tetramethylpiperidin-4-yloxy]-p-xylene; or
bis[1-(2-methoxycarbonylethoxy)-2,2,6,6-tetramethylpiperidin-4-yl] phthalate.

32. A compound of formula IX

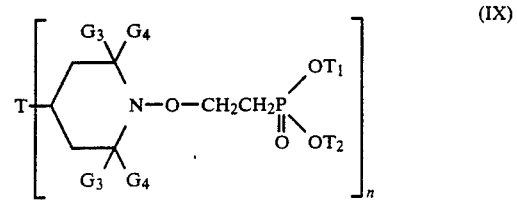

wherein
T is an n-valent radical selected from the group consisting of a carboxyl radical of an aliphatic, cycloaliphatic or aromatic acid, hydroxy, alkoxy, cycloalkoxy, aralkoxy, an aminyl radical of an aliphatic or aromatic primary or secondary amine or of melamine or of an N-substituted melamine, an amidyl radical of an aliphatic or aromatic amide, carbamide or carbamate and an imidyl radical of a saturated imide, or
T is a 2n-valent alkoxy diradical forming a 1,3-dioxolane or 1,3-dioxane ring, or
T is a divalent radical of hydantoin or N-substituted hydantoin or a divalent carbon radical of 2,2-substituted 4-oxazolidone ,
n is 1 to 4,
G$_3$ and G$_4$ are independently alkyl of 1 to 4 carbon atoms, or G$_3$ and G$_4$ together are pentamethylene, and
T$_1$ and T$_2$ are independently hydrogen, alkyl of 1 to 36 carbon atoms, cycloalkyl of 5 to 12 carbon atoms, aralkyl of 7 to 9 carbon atoms or said aralkyl substituted by alkyl of 1 to 36 carbon atoms, or the alkali metal or alkaline earth metal salts thereof.

33. A compound according to claim 32 wherein T is monovalent, n is 1 and G$_3$ and G$_4$ are each methyl.

34. A compound according to claim 32 wherein T$_1$ and T$_2$ are independently alkyl of 1 to 18 carbon atoms, cyclopentyl, cyclohexyl, benzyl, alpha-methylbenzyl or alpha,alphadimethylbenzyl.

35. A compound according to claim 34 wherein T$_1$ and T$_2$ are alkyl of 1 to 8 carbon atoms.

36. The compound according to claim 32 which is diethyl 2-(4-benzoyloxy-2,2,6,6-tetramethylpiperidin-1-oxy)ethylphosphonate.

37. A composition stabilized against the deleterious effects of actinic light which comprises
(a) a synthetic polymer, and
(b) a stabilizing amount of a compound of formula IX according to claim 32.